United States Patent [19]

Grant

[11] Patent Number: 4,919,150
[45] Date of Patent: Apr. 24, 1990

[54] INTRAVENOUS CATHETER SHIELD AND RETAINER

[76] Inventor: Michael L. Grant, P.O. Box 95744, Oklahoma City, Okla. 73143

[21] Appl. No.: 378,359

[22] Filed: Jun. 26, 1989

[51] Int. Cl.$^5$ .............................................. A61M 5/00
[52] U.S. Cl. .................................... 128/877; 220/337; 220/352
[58] Field of Search ......... 128/877, 888, 887, DIG. 6, 128/DIG. 26; 604/174; 220/352, 353, 337, 338

[56] References Cited

U.S. PATENT DOCUMENTS 4,161,261  7/1979  Frater .................................. 220/337
4,576,589  3/1986  Kraus et al. ............ 128/DIG. 26 X

FOREIGN PATENT DOCUMENTS 0266176  5/1988  European Pat. Off. ............ 128/877

Primary Examiner—Robert A. Hafer
Assistant Examiner—Lynda M. Cofsky
Attorney, Agent, or Firm—Robert K. Rhea

[57] ABSTRACT

An intravenous catheter shield is formed by a base underlying a portion of the patient's limb containing an infusion needle. A transparent channel-like housing is hingedly connected with the base and overlies the catheter area in vertical spaced relation. Velcro equipped straps secure the patient's limb to the base and the outer surface of the housing is provided with resilient clamps which grip an IV tube extending across the housing and into its interior for connection with the catheter.

2 Claims, 2 Drawing Sheets

INTRAVENOUS CATHETER SHIELD AND RETAINER

BACKGROUND OF THE INVENTION

1. 1 Field of the Invention

The present invention relates to the field of intravenous catheters and more particularly to a guard or shield for the venipuncture site, a catheter and an intravenous tubing retainer.

When intravenous fluid is to be periodically injected into a patient over an extended time period, it has been the general practice to insert a cannula beneath the surface of the skin into a vein and to retain the cannula in position by adhesive tape. This simple arrangement is effective; however, problems can arise in that the adhesive tape sometimes prevents visual inspection of the puncture site and often provides inadequate retention of the cannula as the patient moves or as the nurse inserts a needle to inject other medication.

Further, the adhesive tape is irritating particularly when the patient is sensitive to the adhesive tape, which causes irritation and creates considerable discomfort for the patient at the area of the intravenous catheter.

2. Description of the Prior Art

Prior patents generally disclose a base member, which may be pan-like in general configuration, which supports a section of intravenous tubing and a catheter and is attached to the arm or leg of the patient by encircling straps.

These devices, are generally satisfactory, but have the disadvantage when used with an active patient, such as a child, they do not provide adequate support for either the tubing or the catheter. One present method of protecting the needle site is the use of a styrofoam cup, severed in half, with the base portion inverted and taped over the needle area or catheter with cloth tape. This sometimes causes the needle to come out, after extended use, such as three or more days, and the skin to become raw. The cloth tape, as stated above, irritates the skin and must be removed to inspect the condition of the patient's vein.

This invention is distinctive over the above described devices by providing a base which supports a portion of the patient's arm or leg by being attached thereto, in underlying relation, by strap members and includes a see-through housing overlying the catheter or intravenous tubular connection or puncture site of the patient's vein.

The see-through housing also supports the adjacent end portion of the intravenous tubing to prevent movement of the tubing, particularly at its end portion connected with the catheter.

SUMMARY OF THE INVENTION

An elongated rigid board-like member of selected length and width underlies a section of the patient's arm and is attached thereto as by hook and eye Velcro equipped straps extending transversely across the patient's limb and connected with opposing side portions of the base member.

At least one, preferably two members, inverted U-shaped in cross section, span the patient's arm and hand in longitudinal relation, with respective side edge portions of the housing attached in a removable fashion to respective side edge portions of the base member. At least one, preferably both ends of the housing allow the intravenous tubing to enter the housing, above the patient's arm or hand and be connected with a previously installed catheter. The tubing extending out of the housing and longitudinally thereof, being secured thereto by frictional clips or clamps on the exterior of the housing.

The principal object of this invention is to provide a transparent shield for a catheter and a retainer for intravenous tubing, which permits visual inspection of the catheter site, without disassembling or removing any covering, such as tape or other material concealing the catheter and which will prevent movement of the intravenous tubing relative to the catheter, thus insuring a relatively long useful life of the vein puncturing position of the catheter.

DESCRIPTION OF THE PREFERRED EMBODIMENTS

Figure 1:
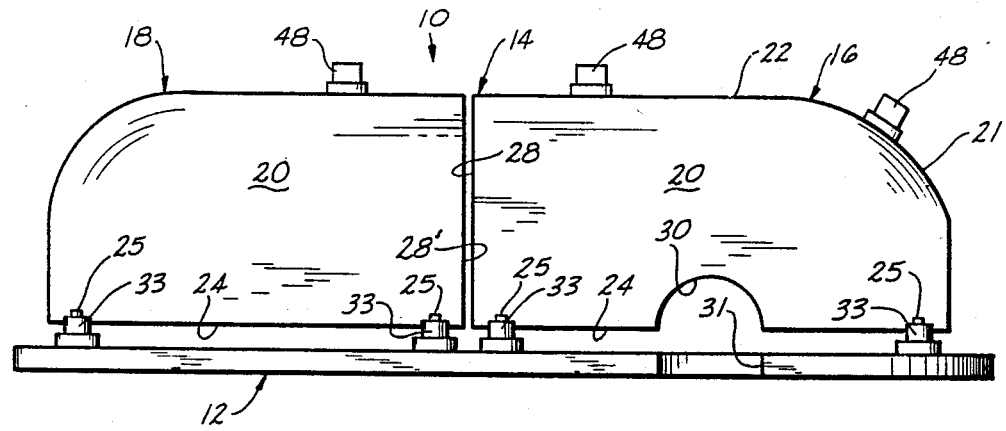
FIG. 1 is a side elevational view of the device.
Figure 2:
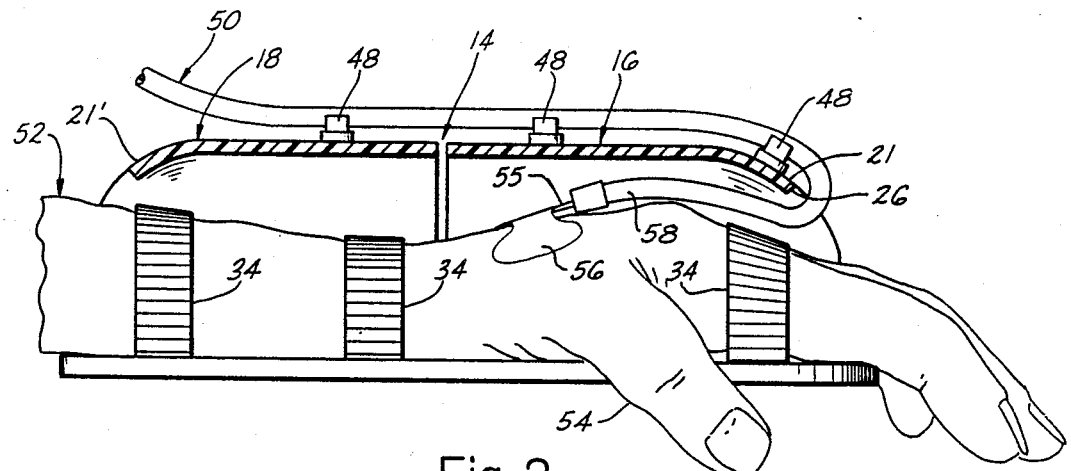
FIG. 2 is a view similar to FIG. 1, illustrating the device installed on a patient's forearm and hand, the housing being shown in vertical cross-section.
Figure 3:
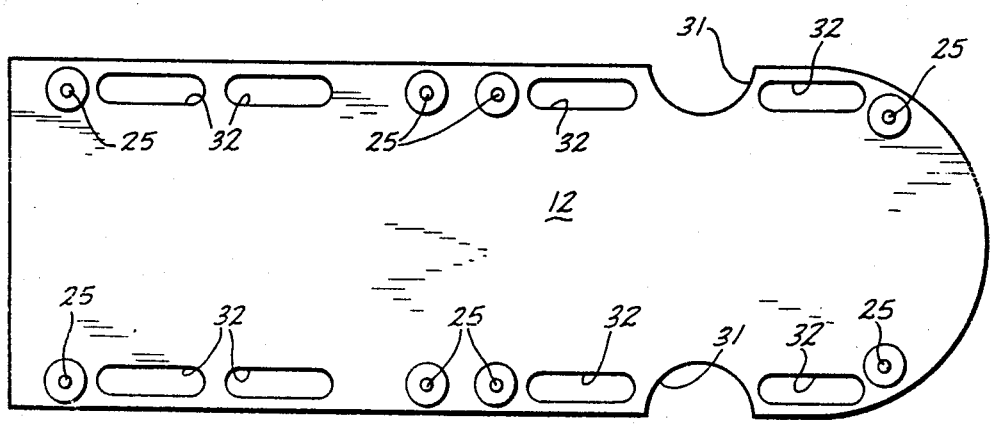
FIG. 3 is a top view of the base of the device.
Figure 4:
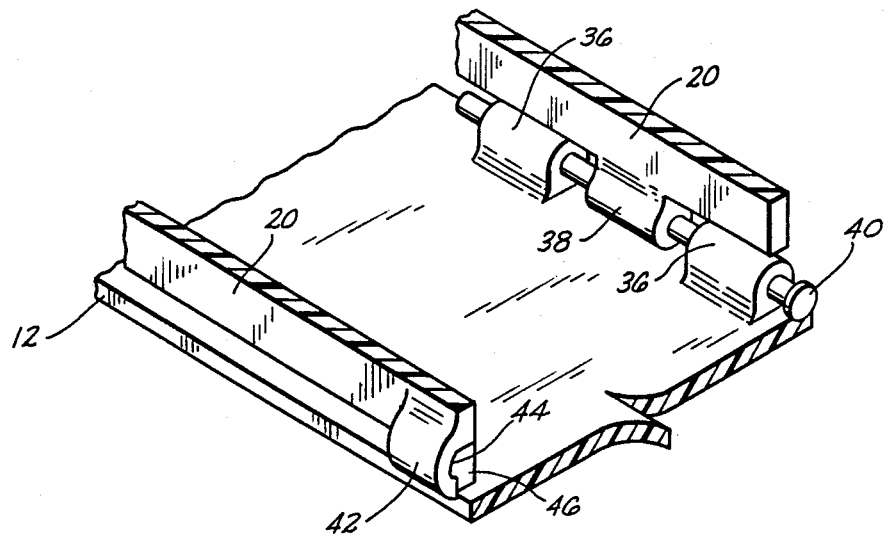
FIG. 4 is a fragmentary perspective view illustrating the manner of connecting the housing to its base.

Like characters of reference designate like parts in those figures of the drawings in which they occur.

In the drawings:

The reference numeral 10 indicates the device as a whole, which is U-shaped channel in general configuration, comprising a flat base 12 and a transparent housing means 14 overlying the base. The base forms a limb immobilizing member and is of a selected length and width to underlie a portion of a patient's limb, such as a forearm or lower end portion of a leg.

The housing means 14, comprises elongated forward and rearward sections 16 and 18, substantially mirror images of each other and are assembled on the base in end to end relation. The forward housing 16 includes generally parallel upstanding wall portions 20 and an arcuate forward surface 21, merging rearwardly into a horizontal top surface 22.

The housing forward arcuate surface 21 terminates in spaced relation with respect to the bottom edges 24 of the housing to form a forward opening 26, for the reason presently apparent, substantially equal in height with the width of the base 12. The rearward end 28 of the forward housing describes a generally vertical plane normal to the plane of the base 12 and is disposed substantially medially the length of the base.

As stated above the rearward housing 18 is substantially identical to the forward housing with its rearward arcuate surface 21' projecting opposite the forward housing arcuate surface 21 and its forward vertical surface 28' disposed in close spaced relation with respect to the forward housing rearward edge 28.

The forward housing 16 is distinctive over the rearward housing 18 by an inverted, generally U-shaped recess 30 in its opposing lower edge surfaces 24, spaced rearwardly of its forward end, and cooperatively disposed above similar U-shaped recesses 31 cooperatively formed in the opposing side edges of the base 12 for the purpose of loosely surrounding a portion of the thumb of a patient as hereinafter described.

Adjacent each of its lateral longitudinal edges the base 12 is provided with a plurality of upstanding pins 25 which project above the top surface of the base a selected distance. Each of the housings 16 and 18 is also provided, adjacent its respective depending lateral edge 24, with a plurality of sleeves 33 each having a vertical opening which cooperatively surrounds and frictionally grips the upstanding top portion of the pins 25 for removably securing the housings 16 and 18 to the base.

The base 12 is provided with a plurality of longitudinally extending slots 32 adjacent its respective longitudinal side edges for the purpose of receiving straps 34 of a selected length for securing a patient's arm to the base. The straps 34 are preferably provided with or are formed from material having a self-adhering fabric material thereon, presently marketed under the tradename Velcro, which is generally commercially available in fabric or department stores. The Velcro material comprises two mating portions. One portion has a large number of tiny filament eyelets extending from a base sheet of fabric, the second portion has a large number of small elastic hook projections adapted to engage the eyelets of the other portion when a manual force is applied thereto for separably joining the two strap ends 34 by the engagement of the hook and eye mating portions of the Velcro.

The base 12 is preferably provided adjacent one of its side edges with hinge means comprising a plurality of longitudinally spaced hinge pin receiving loops 36. Similarly the adjacent depending edge surface of each housing section 16 and 18 is provided with cooperating, hinge pin receiving loops 38, so that the hinge loops 36 and 38 are disposed in inter-digitated relation when the respective housing section overlies the base 12. The hinge loops are axially aligned for removably receiving a hinge pin 40 for the purpose of vertical pivoting movement, about a horizontal axis, of each housing section toward and away from the upwardly disposed surface of the base 12.

The opposite depending edge portion of each housing is provided with at least one depending hook portion 42, having a recess 44, cooperatively engaging an upstanding, substantially inverted J-shaped hook member 46 projecting above the upper surface of the base 12 on that side opposite the hinge means for the purpose of temporarily holding each section attached to the base 12 in combination with the hinge means.

The housings 16 and 18 are provided on their respective upper surface with a plurality of longitudinally spaced upstanding spring material clamps members 48, U-shaped in transverse section, which removably receive and frictionally hold an intermediate portion of a length of intravenous tubing 50. One of the clamp members 48 being disposed on the forward arcuate surface 21 of the forward housing 16, so that the tubing 50 may project at its needle communicating end through the opening 26 for the purposes presently explained.

OPERATION

In operation the base 12 is positioned under the limb of a patient to contain a catheter for intravenous injections, such as the forearm 52. The base 12 is preferably positioned so that the patient's thumb 54 may overhang the base within the lateral notch 31 therein for comfort. The Velcro equipped straps 34 extending through the base slots 32 are transversely extended across the patient's forearm with preferably one of the straps forwardly and rearwardly, respectively, of the position of a catheter 55, such as an intravenous needle inserted into a patient's vein, not shown, normally secured in place as by a relatively short section of tape 56, in a conventional manner.

The intravenous tube end portion 58 is then placed in operative contact with the catheter or needle. The forward housing 16, if not previously hingedly attached to the base 12, is placed thereon and the hinge 40 pin manually extended through the apertures of the hinge loops 36 and 38. The housing then is pivoted over the patient's hand and finger portion and clipped into place at the opposite side of the base. Similarly the rearward housing 18, if used, is attached in a position rearwardly of the forward housing 16 in the manner described for the housing 16. The intravenous tubing 50 then being strung through the several U-shaped clamps 48 holding the tubing 50 in place. The transparent material, from which at least the forward housing 16 is constructed, permits the nurse, patient or other persons to readily visualize the condition of the catheter and its position without necessitating removing dressings as mentioned hereinabove. The housing 16 is easily manually released from the base for changing the tubing or connecting another IV tube with the catheter as desired.

Obviously the invention is susceptible to changes or alterations without defeating its practicability. Therefore, I do not wish to be confined to the preferred embodiment shown in the drawings and described herein.

I claim:

1. A shield for protecting the position of an intravenous needle having a supply tube connected at one end thereto when the needle is inserted in a body part of a patient, comprising:

an elongated generally rectangular planar base for underlying the terminal end portion of a patient's limb, said base having a plurality of elongated slots adjacent opposing longitudinal side edges;

flexible means for securing said base to the patient's limb in an immobilizing manner, said flexible means including, a like plurality of elongated straps respectively extending through said plurality of slots and surrounding a portion of said base and patient's limb thereon, each strap of said plurality of straps having opposing end portions disposed in overlapping relation;

self-adhering fabric material cooperatively secured to said strap opposing end portions for releasably joining said end portions together;

a rigid inverted open end channel-like transparent housing substantially U-shape in transverse cross section having coextensive depending leg portions and an arcuate bight portion longitudinally overlying the base in laterally and vertically spaced relation with respect to the surface of the patient's limb and an intravenous needle position;

means releasably securing the housing leg portions to respective side edge portions of said base, said housing releasable means including, an upstanding pin adjacent respective opposing longitudinal side edges of said base and, a vertically apertured lug adjacent the depending limit of the housing respective leg portion for cooperative frictional reception of said pin; and, spring clamp means on said housing for securing one end portion of a needle supply tube to said housing.

2. A shield for protecting the position of an intravenous needle having a supply tube connected at one end thereto when the needle is inserted in a body part of a patient, comprising:

an elongated generally rectangular planar base for underlying the terminal end portion of a patient's limb;, flexible means for securing said base to the patient's limb in an immobilizing manner;

a rigid inverted open end channel-like transparent housing substantially U-shape in transverse cross section having co-extensive depending leg portions and an arcuate bight portion longitudinally overlying the base in laterally and vertically spaced relation with respect to the surface of the patient's limb and an intravenous needle position;

means releasably securing the housing leg portions to respective side edge portions of said base, said housing releasable means including,
an upstanding pin adjacent respective opposing longitudinal side edges of said base,
a vertically apertured lug adjacent the depending limit of the housing respective leg portion for cooperative frictional reception of said pin; and, spring clamp means on said housing for securing one end portion of a needle supply tube to said housing.

* * * * *